(12) United States Patent
Edwards

(10) Patent No.: US 6,692,490 B1
(45) Date of Patent: *Feb. 17, 2004

(54) TREATMENT OF URINARY INCONTINENCE AND OTHER DISORDERS BY APPLICATION OF ENERGY AND DRUGS

(75) Inventor: Stuart D. Edwards, Portola Valley, CA (US)

(73) Assignee: Novasys Medical, Inc., Newark, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/407,658

(22) Filed: Sep. 28, 1999

Related U.S. Application Data

(60) Provisional application No. 60/134,672, filed on May 18, 1999.

(51) Int. Cl.⁷ ............................................. A61B 18/18
(52) U.S. Cl. ........................... 606/41; 606/42; 607/101; 607/105
(58) Field of Search .............................. 606/32, 41, 42, 606/45, 47, 48–50; 607/41, 100, 101, 102, 104, 105; 604/22

(56) References Cited

U.S. PATENT DOCUMENTS

| | | | |
|---|---|---|---|
| 5,836,874 A | * | 11/1998 | Swanson et al. ............. 600/374 |
| 5,871,469 A | * | 2/1999 | Eggers et al. ................ 604/114 |
| 5,921,982 A | * | 7/1999 | Lesh et al. ..................... 606/41 |
| 5,961,513 A | * | 10/1999 | Swanson et al. .............. 606/34 |
| 5,971,983 A | * | 10/1999 | Lesh ............................. 606/41 |
| 6,231,570 B1 | * | 5/2001 | Tu et al. ........................ 606/41 |
| 6,231,591 B1 | * | 5/2001 | Desai ............................. 604/8 |
| 6,500,175 B1 | * | 12/2002 | Gough et al. .................. 606/42 |

* cited by examiner

Primary Examiner—Rosiland K. Rollins
(74) Attorney, Agent, or Firm—Glenn Patent Group; Michael A. Glenn

(57) ABSTRACT

The invention provides a method and system for treating disorders of the genito-urinary tract and other disorders in other parts of the body. A particular treatment can include one or more of, or some combination of ablation, nerve modulation, three-dimensional tissue shaping, drug delivery, mapping, stimulating, shrinking (by creation of a pattern of thermal lesions) and reducing strain on structures by altering the geometry thereof and providing bulk to particularly defined regions. The particular body structures or tissues can include one or more of, or some combination of regions, including the bladder, esophagus, vagina, penis, larynx, pharynx, aortic arch, abdominal aorta, thoracic aorta, large intestine, small intestine, sinus, auditory canal, uterus, vas deferens, trachea and all associated sphincters. In one aspect of the invention, a catheter is deployed in the body. It may enter the body via a natural orifice, a stoma, or a surgically created opening that is made for the purpose of inserting the catheter. Insertion may be facilitated with the use of a guide wire or a generic support structure or visualization apparatus. In second aspect of the invention, the treatment can include application of energy and substances to effect changes in the target tissue. Types of energy that can be applied include radiofrequency, laser, microwave, infrared waves, ultrasound or some combination thereof. Types of substances that can be applied include pharmaceutical agents such as analgesics, antibiotics and anti-inflammatory drugs, bulking agents such as biologically nonreactive particles, cooling fluids or dessicants such as liquid nitrogen for use in cryo-based treatments.

23 Claims, 9 Drawing Sheets

From FIG. 2A

215 — The enrgy port is manipulated so as to cause a release of energy from electrodes 119. This is similar to step 211 and 213. The lesions effected in all three of these steps have the effect of shrinking the trigone area so as to relieve pressure on the bladderneck. The three dimensional geometry is altered and the scar tissue created by the application of energy is stronger and better able to resist abdominal pressure.

216 — The irrigation and control port 135 is manipulated so as to stop the flow of cooling liquid from the aperture 118. Suction may be applied to remove excess cooling liquid.

217 — Pharmaceutical agents may be locally administered by manipulating the irrigation and aspiration control ports.

218 — The catheter 110 is withdrawn from the urethra.

FIG. 2B

From FIG. 4A

414 — The energy port 336 is manipulated so as to cause a release of energy from the electrodes 322 that were identified in step 412. Partial or complete ablation of these nerves may affect incontinence caused by an uncontrollable urge to urinate. This step is optional.

415 — Bulking agents or microspheres are exuded from selected electrodes 322 positioned near the base of the bladder. These bulking agents can be used to strengthen the structure to prevent stress incontinence.

416 — Pharmacological agents may be locally administered by manipulating the irrigation and aspiration control ports 335. This step may occur any time prior to withdrawal of catheter 310, thereby causing the balloon to deflate.

417 — The irrigation and aspiration control port 335 is manipulated so as to reverse the flow of cooling liquid from the microporous treatment balloon 320, thereby causing the balloon to deflate.

418 — The catheter 310 is withdrawn from the urethra.

FIG. 4B

From FIG. 6A

615 — The energy port 536 is manipulated so as to cause a release of energy from the electrodes 522 that is directed at the nerves that were identified in step 613. Partial or complete ablation of these nerves may treat incontinence caused by an uncontrollable urge to urinate. This step is optional.

616 — Bulking agents such as organic microspheres, collagens, silicon and other polymers are exuded from the selected electrodes 522 positioned near the base of the bladder.

617 — Pharmacological agents may be locally administered by manipulating the aspiration control ports 535. This step may occur at any time prior to withdrawal of the catheter 510.

618 — The irrigation and aspiration control port 535 is manipulated so as to reverse the flow of cooling liquid.

619 — Tension is applied to the translation member 512 to cause the umbrella-like struts 521 to collapse and close around the catheter 510 and the translation member 512.

620 — The catheter 510 is withdrawn from the urethra.

FIG. 6B

TREATMENT OF URINARY INCONTINENCE AND OTHER DISORDERS BY APPLICATION OF ENERGY AND DRUGS

RELATED APPLICATIONS

Inventions described herein can be used in combination or conjunction with inventions described in the following patent application(s):

Application Ser. No. 08/731,372, filed Oct. 11, 1996, claiming priority dates at least as early as Jun. 24, 1994, in the name of Stuart D. Edwards, and all pending cases claiming priority thereof;

Application Ser. No. 09/026,316, filed Feb. 19, 1998, in the name of Stuart D. Edwards, and all pending cases claiming priority thereof;

Application Ser. No. 08/677,811, filed Jul. 10, 1996, in the name of Lawrence J. Mohr, Jr., and Stuart D. Edwards, titled "Treating Aneurysms by Applying Hardening/Softening Agents to Hardenable/Softenable Substances," attorney docket number MOED-001, and all pending cases claiming priority thereof;

Application Ser. No. 08/717,612, filed Sep. 20, 1996, in the name of Stuart D. Edwards and Steven Marcus, titled "Ablation of Rectal and Other Internal Body Structures," assigned to the same assignee, attorney docket number VCAR-001, and all pending cases claiming priority thereof;

Application Ser. No. 08/795,656, filed Feb. 6, 1997, in the name of Stuart D. Edwards and Muta M. Issa, titled "Treating Urinary and Other Body Structures," assigned to the same assignee, attorney docket number VCAR-002, and all pending cases claiming priority thereof;

Application Ser. No. 09/285578, filed Apr. 2, 1999, in the name of Stuart D. Edwards, titled "Treating Body Tissue by Applying Energy and Substances", assigned to the same assignee, attorney docket number VCAR-006, and all pending cases claiming priority thereof;

Application Ser. No. 09/307348, filed May 6, 1999, in the name of Stuart D. Edwards, titled "Treatment of Tissue in the Digestive, Circulatory, Respiratory, Urinary and Reproductive Systems" assigned to the same assignee, attorney docket number VCAR-010, and all pending cases claiming priority thereof;

Provisional Application Ser. No. 60-134672, filed May 18, 1999, in the name of Stuart D. Edwards, titled "Surgical Weight Control Device", assigned to the same assignee, attorney docket number VCAR-015, and all pending cases claiming priority thereof; and Application Ser. No. 09/339473, filed Jun. 23, 1999, in the name of Stuart D. Edwards, titled "Treating Body Tissue by Applying Energy and Substances with a Retractable Catheter and Contained Cooling Element", assigned to the same assignee, attorney docket number VCAR-009, and all pending cases claiming priority thereof.

These applications are each hereby incorporated by reference as if fully set forth herein. These applications are collectively referred to herein as "Incorporated Disclosures."

BACKGROUND OF THE INVENTION

1. Field of the Invention

This invention relates to treating body tissue, particularly to treating body tissue by altering the shape, density, relative geometry or tension of that body tissue using energy or substances deployed from an interstitial location in the body.

2. Related Art

Urinary incontinence results from a number of factors. Increasing age, injury from childbirth and related stresses can cause the relative tone of the bladder and accessory muscles to weaken, which, in turn, causes an impaired ability to retain urine. Weight gain and overall deterioration of muscle tone can cause increased abdominal pressure which overcomes sphincter resistance. Nerve pathways that cause the "urge" to urinate can become hyperactive. The relative tension of the urethra can change with age, causing poor urinary control. Injury to the detrusor muscles or to the trigone area also results in impaired urinary continence.

These factors do not usually occur by themselves. The typical patient usually presents with two or more of them. Therefore, it is desirable to provide a treatment that can address many of these factors.

Given the complex etiology and varied causal factors, the ideal treatment for urinary incontinence requires a device that can perform many different functions. For example, a treatment for female urinary incontinence might rely upon some or all of the following: (1) reshaping the bladder to alter the urethrovesical angle and resuspend the bladderneck, (2) manipulation of the detruser muscles, (3) mapping and modulating nervous pathways responsible for urinary urgency, (4) reducing strain on the bladderneck by changing the structural geometry, (5) shrinking discrete and non-discrete areas of the bladder by creating thermal lesions, (6) three-dimensional modeling of tissue by adding bulk so as to achieve better closure (7) strengthening the structural integrity of a tissue by providing a pattern of scar tissue and (7) application of pharmaceutical agents both as a curative and to promote healing post treatment.

The use of a catheter to apply radio frequency (RF) and other types of energy to ablate tissue in the body (such as heart muscle tissue) is known in the art of cardiac treatment. However, known systems using RF and other types of energy are still subject to several drawbacks.

A first problem in the known art involves providing a device that can perform all of the aforementioned functions. While known systems can perform one or more of these functions, nothing in the related art is capable of performing all of these functions. Patients are frequently required to return for multiple treatments until a cure is finally effected.

A second problem in the known art involves identification, modulation and/or stimulation of nerves in the targeted tissue. Known systems do not provide for protection of sensitive nerves during treatment or allow nerves to be identified and stimulated. This is particularly problematic because many tissue disorders, especially those involving tone or contractile ability of a sphincter, arise from afferent and efferent nerves are either under-stimulated or over-stimulated.

A third problem in the known art involves providing a treatment surface that can reach all of the desired treatment areas, such as the entire surface of the detrusor muscles. While the use of a catheter to deploy energy is known, none is disposed to flexibly adapt to the interior shape of an organ so as to provide optimal uniform treatment.

A fourth problem in the known art involves removal of tissue and substances used in treatment. Known systems do not provide for removal of excess substances used in treatment such as cooling fluids, collagen or bulking substances. Similarly, known systems do not provide for removal of substances that hinders or otherwise obstructs the healing process such as pus, purulent discharges, suppuration and pockets of infection.

A fifth problem in the known art involves directing and positioning the electrodes in the body cavity or orifice. Difficulties in accurately positioning the electrodes in the target orifice detract from treatment. Frequently, unhealthy tissue remains untreated while healthy tissue is compromised. Difficulties in directing and positioning the electrodes are particularly problematic because one of the goals of treatment is to minimize collateral damage to healthy tissue and to completely treat diseased tissue.

A sixth problem in the known art involves minimizing thermal injury to the patient. Some known systems rely upon simultaneous application of energy and infusion of a cooling liquid into the targeted area for treatment. While such infusion of liquid minimizes thermal injury to the patient, it is not applicable to all parts of the body. For example, infusion of cooling liquids into an internal body cavity such as a bladder, uterus, or stomach can rupture the targeted organ or cause osmotic imbalance within the tissue.

A seventh problem in the known art involves difficulty in the simultaneous use of complimentary technology. Known systems do not provide for optimal, simultaneous use of auxiliary tools for visualization, monitoring pH and pressure or drug administration.

A eighth problem in the known art is that it can be difficult to block the flow of bodily fluids and gases into an area of the body where tissue ablation is taking place. Bodily fluids can dissipate and detrimentally absorb the energy to be applied to the tissue to be ablated. Dissipation of bodily fluids detracts from the goal of treatment of diseased tissue.

Accordingly, it would be advantageous to provide a method and apparatus for treatment for body structures, especially internal body structures involving unwanted features or other disorders, that does not require relatively invasive surgery, and is not subject to other drawbacks noted with regard to the known art. This advantage is achieved in an embodiment of the invention in which a relatively minimally invasive catheter is inserted into the body, a variety of different treatments of the body structures is applied using electrodes and a cooling element, and the unwanted features or disorders are relatively cured.

SUMMARY OF THE INVENTION

The invention provides a method and system for treating disorders of the genito-urinary tract and other disorders in other parts of the body. A particular treatment can include one or more of, or some combination of ablation, nerve modulation, three-dimensional tissue shaping, drug delivery, mapping, stimulating, shrinking (by creation of a pattern of thermal lesions) and reducing strain on structures by altering the geometry thereof and providing bulk to particularly defined regions.

The particular body structures or tissues can include one or more of, or some combination of regions, including the bladder, esophagus, vagina, penis, larynx, pharynx, aortic arch, abdominal aorta, thoracic aorta, large intestine, small intestine, sinus, auditory canal, uterus, vas deferens, trachea and all associated sphincters.

In one aspect of the invention, a catheter is deployed in the body. It may enter the body via a natural orifice, a stoma, or a surgically created opening that is made for the purpose of inserting the catheter. Insertion may be facilitated with the use of a guide wire or a generic support structure or visualization apparatus.

In second aspect of the invention, the treatment can include application of energy and substances to effect changes in the target tissue. Types of energy that can be applied include radiofrequency, laser, microwave, infrared waves, ultrasound or some combination thereof. Types of substances that can be applied include pharmaceutical agents such as analgesics, antibiotics and anti-inflammatory drugs, bulking agents such as biologically nonreactive particles, cooling fluids or dessicants such as liquid nitrogen for use in cryo-based treatments.

DETAILED DESCRIPTION OF THE PREFERRED EMBODIMENT

In the following description, a preferred embodiment of the invention is described with regard to preferred process steps and data structures. Embodiments of the invention can be implemented using general-purpose processors or special purpose processors operating under program control, or other circuits, adapted to particular process steps and data structures described herein. Implementation of the process steps and data structures described herein would not require undue experimentation or further invention.

Figure 1:
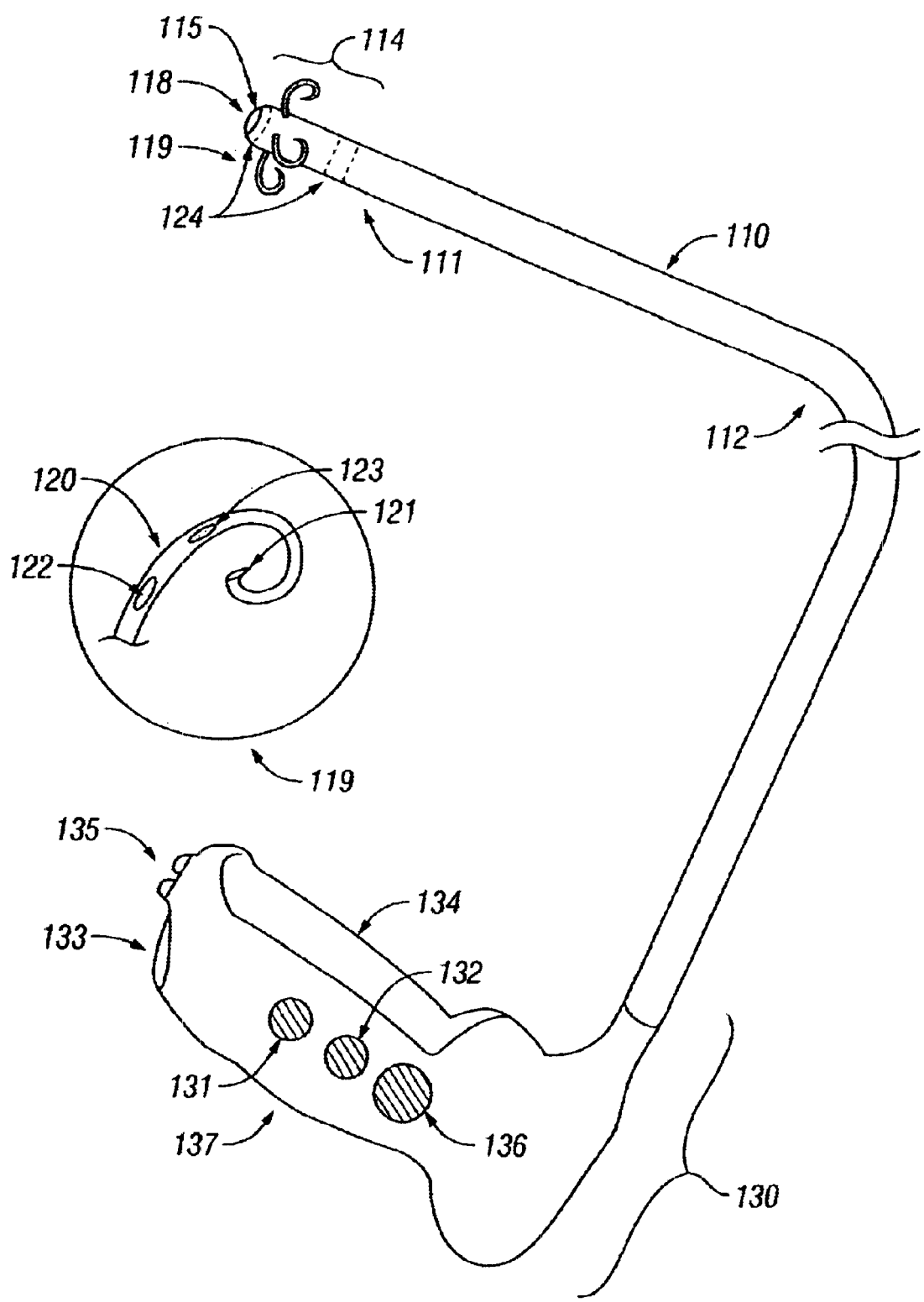
FIG. 1 is a block drawing of a system for treatment of female urinary incontinence using a first device.

FIG. 1 is a block drawing of a system for treatment of female urinary incontinence using a first device.

A system 100 includes a catheter 110, a treatment element 114, a control assembly 130 and a shielding element 140. In an alternative embodiment, the shielding element 140 is not present.

The Catheter

The catheter 110 includes a distal segment 111 and a proximal segment 112. The distal segment 111 and proximal segment 112 form one continuous piece. Two or more lumens 113 (not shown) run the entire interior length of the catheter 110 and are coupled to the control assembly 140. It is through these lumens 113 that energy is conducted and flowable substances are exuded.

The distal segment 111 includes a treatment element 114 and a tapered tip 115. In a preferred embodiment, the tapered tip 115 is rigid so as to allow easy insertion into a urethra. In other preferred embodiments, the tapered tip 115 may be of varying degrees of flexibility depending where it in the body it is deployed. In alternative embodiments, the catheter 110 may be introduced into the target tissue using an introducer sheath 116 or a guide wire 117 (not shown). The most distal end of the tapered tip 115 includes an aperture 118. Substances that flow through the lumens 113 may be applied to the tissue through this aperture 118.

In a preferred embodiment, the distal segment 111 is disposed for insertion into a cavity of the body such as a female urethra and bladder. In alternative embodiments, the cavity may include one or more of, or some combination of the following:

Any portion of the bronchial system, the cardiovascular system, the genito-urinary tract, the lymphatic system, the pulmonary system, the vascular system, the locomotor system, the reproductive system or other systems in the body;

Any biological conduit or tube, such as a biologic lumen that is patent or one that is subject to a stricture;

Any biologic operational structure, such as a gland, or a muscle or other organ (such as the colon, the diaphragm, the heart, a uterus, a kidney, a lung, the rectum an involuntary or voluntary sphincter);

Any biologic structure, such as a herniated body structure, a set of diseaseed cells, a set of displastic cells, a surface of a body structure, (such as the sclera) a tumor, or a layer of cells (such as fat, muscle or skin).

Any biologic cavity or space or the contents thereof, such as a cyst, a gland, a sinus, a layered structure, or a medical device implanted or inserted in the body;

The Treatment Element

The treatment element 114 includes a set of curvilinear electrodes 119 and three sets of irrigation and aspiration ports 124.

The electrodes 119 contained in the set of electrodes are evenly spaced around the tapered tip 115. Each electrode 119 includes a metallic tube 120 defining a hollow lumen 121 and is disposed so that it curves away from the tapered tip 115 and has a barbed end, much like a fishhook. Being arced in this direction allows the device to be inserted easily into an orifice without causing unintended tissue damage. Once the device is inserted, the barbed ends of electrodes 119 grab the tissue of the bladderneck and upper urethra in a claw-like manner and bunch it together. Energy is delivered through the electrodes to the bunched tissue, causing shrinkage to occur in the area surrounding the treatment element 114. This three dimensional shaping improves continence by improving the structural integrity of the tissue.

In a preferred embodiment, there are four electrodes 119. Other preferred embodiments may have more or less than four electrodes. Each electrode 119 is coupled to at least one sensor 122 capable of measuring such factors as temperature, conductivity, pressure, impedance and other variables. In a preferred embodiment, each electrode is also coupled to a radiopaque marker 123 for use in fluoroscopic visualization.

In a preferred embodiment, the electrodes 119 can be operated separately or in combination with each other as sequences of electrodes disposed in arrays. Treatment can be directed at a single area or several different areas of a bladder or other orifice by operation of selective electrodes. Different patterns of submucosal lesions, mucosal lesions, ablated, bulked, plumped, desiccated or necrotic regions can be created by selectively operating different electrodes. Production of different patterns of treatment makes it possible to remodel tissues and alter their overall geometry with respect to each other.

Each electrode 119 can be disposed to treat tissue by delivering one or more of, or some combination or any of the following in either a unipolar or bipolar mode:

Radiofrequency (RF) energy, such as RF in about the 300 kilohertz to 500 kilohertz range;

Chemical treatments, such as acids, antibiotics, enzymes, radioactive tracers or other bioactive substances;

Infrared energy, such as from an infrared laser or diode laser;

Microwave energy, such as electromagnetic energy in about the 915 megahertz or 2.45 gigahertz range;

Sonic energy, including ultrasound;

Photodynamic therapy (PDT)

Non-infrared laser energy

Cryothermia

In addition to treating tissues by delivering energy, the set of electrodes 119 are disposed to deliver at least one flowable substance to the area of the body where treatment is to take place. In a preferred embodiment, the flowable substance includes water which aids in cooling of body structures during RF application. However, in alternative embodiments, the deliverable flowable liquids include other substances, including saline, anesthetic drugs, anti-inflammatory agents, chemotherapeutic agents, systemic or topical antibiotics, collagen and radioactive substances such as labeled tracers. In one alternative embodiment, saline is used to increate the local conductivity of tissue, enhancing the penetration of RF energy so as to create larger lesions. The saline can be delivered through the needle electrode submucosally so as to achieve greatest effect.

Three rings of irrigation and aspiration ports 124 circle the distal end of the catheter 110. Each ring contains numerous irrigation and aspiration ports 124, evenly distributed around the width of the catheter. One ring of irrigation and aspiration ports 124 lies between the aperture 118 and the set of electrodes 119; the other two rings of irrigation and aspiration ports 124 are located on the proximal side of the electrodes 119. Application of positive pressure makes irrigation and cooling of tissues is possible. Alternatively, application of negative pressure causes the tissue to be uniformly conformed around the treatment element 114, thereby achieving the most optimal therapeutic value of the energy and substances.

The Control Assembly 130

The control assembly 130 includes a visualization port 131, an apparatus port 132, an electrical energy port 133, an electrode selection and control switch 134, one or more irrigation and aspiration control ports 135, an therapeutic energy port 136 and a handle 137.

The visualization port 131 can be coupled to visualization apparatus, such as fiberoptic device, flouroscopic device, an anoscope, a laparoscope, an endoscope or other type of catheter.

The apparatus port 132 can be coupled to other medical devices that may be useful during treatment such as a pH meter, a pressure monitor, drug administration apparatus, or other device used to monitor or treat the patient.

In a preferred embodiment, devices coupled to both the visualization port 131 and the apparatus ports 132 are controlled from a location outside the body, such as by an instrument in an operating room or an external device for manipulating the inserted catheter 110.

In an alternative embodiment the apparatus port 132 may be coupled to devices that are implanted or inserted into the body during a medical procedure. For example, the apparatus port 132 may be coupled to a programmed AICD (artificial implanted cardiac defibrillator), a programmed glandular substitute (such as an artificial pancreas) or other device for use during surgery or other medical procedures.

The electrical energy port 133 includes a conductive element such as an electrical adapter that can be coupled to a source of alternating or direct current such as a wall socket, battery or generator.

The electrode selection and control switch 134 includes an element that is disposed to select and activate individual electrodes 119.

The irrigation and aspiration control ports 135 can be coupled to a pump or other apparatus to deliver fluid through the aperture 118 or apply suction through the set of irrigation and aspiration ports 134.

The therapeutic energy port 136 includes a receptor port for coupling to a source of any of the following types of therapeutic energy:

Radiofrequency (RF) energy, such as RF in about the 300 kilohertz to 500 kilohertz range;

Chemical treatments, such as acids, antibiotics, enzymes, radioactive tracers or other bioactive substances;

Infrared energy, such as from an infrared laser or diode laser;

Microwave energy, such as electromagnetic energy in about the 915 megahertz to 2.45 gigahertz range;

Sonic energy, including ultrasound;

Photodynamic therapy (PDT)

Non-infrared laser energy

Cryothermia

The handle 137 is disposed for manipulated by medical or veterinary personnel and can be shaped for being held in the hand. The visualization port 131, the apparatus port 132, the electrical energy port 133, the electrode selection and control switch 134 and the one or more irrigation and aspiration control ports 135 and the therapeutic energy port 136 are all mounted in the handle 137 to allow for easy operation.

The Shielding Element

A shielding element 140, such as an inflatable balloon, a sponge or a polymer shield, lies on the proximal side of treatment element 114 and is disposed to isolate the treatment area. It can also help position the catheter 110 in the body. For example, in a preferred embodiment in which the catheter 110 is inserted into the urethra, the shielding element 140 can prevent the catheter 110 from being inserted further into the urethral canal and prevent substances used in treatment from escaping.

Figure 2A:
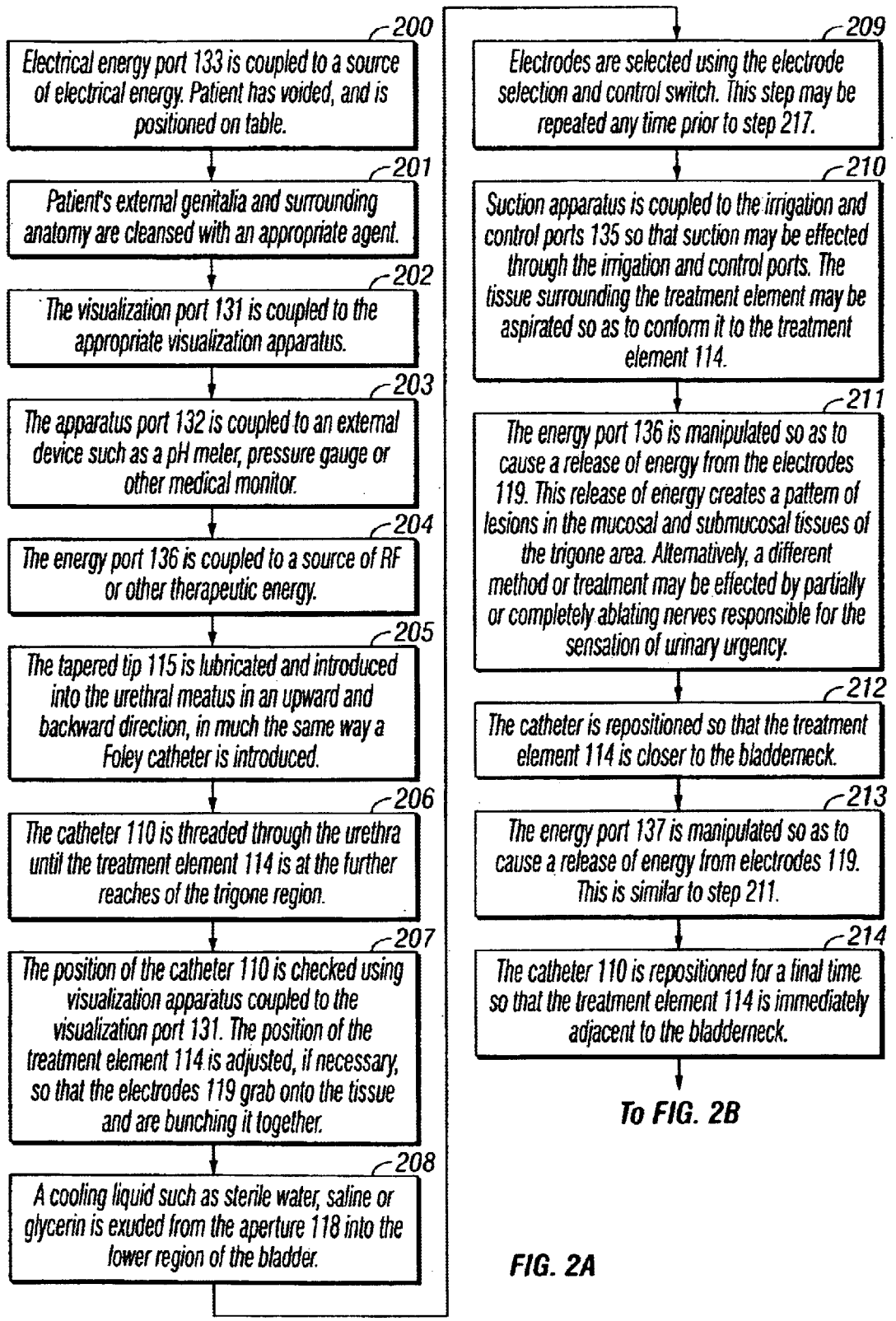
FIG. 2 is a process flow drawing of a method for treatment of female urinary incontinence using a first device.

FIG. 2 is a process flow drawing of a method for treatment of female urinary incontinence using a first device.

A method 200 is performed by a system 100, including a catheter and a control assembly 130. Although the method 200 is described serially, the steps of the method 200 can be performed by separate elements in conjunction or in parallel, whether asynchronously, in a pipelined manner, or otherwise. There is no particular requirement that the method 200 be performed in the same order in which this description lists the steps, except where so indicated.

At a flow point 200, electrical energy port 133 is coupled to a source of electrical energy. The patient has voided and is positioned on a treatment table, in an appropriate position such as horizontal, jackknife or lithotomy. Due to the potential for inducing pain, the area surrounding the urinary meatus may be pretreated with a topical anesthetic before insertion of the catheter 110; depending upon the circumstances, a muscle relaxant or short term tranquilizer may be indicated. The position of the patient and choice of pharmaceutical agents to be used are responsive to judgments by medical personnel.

At a step 201, the patient's external genitalia and surrounding anatomy are cleansed with an appropriate agent such as Betadine, or benzalkonium chloride At a step 202, the visualization port 131 is coupled to the appropriate visualization apparatus, such as a flouroscope, an endoscope, a display screen or other visualization device. The choice of visualization apparatus is responsive to judgments by medical personnel.

At a step 203, the apparatus port 132 is coupled to an external medical device such as a pH meter, a pressure gauge, or other such equipment. The choice of apparatus is responsive to judgments by medical personnel.

At a step 204, the therapeutic energy port 136 is coupled to a source of any of the aforementioned types of therapeutic energy.

At a step 205, the tapered tip 115 is well lubricated and introduced into the urethral meatus in an upward and backward direction, in much the same way a Foley catheter 110 is introduced.

In a step 206, the catheter 110 is threaded through the urethra until the treatment element 114 is at the further reaches of the trigone region. An introducer sheath 116 or guidewire 117 may also be used to facilitate insertion.

In a step 207, the position of the catheter 110 is checked using visualization apparatus coupled to the visualization port 131. The position of the treatment element 114 is adjusted, if necessary, so that the electrodes 119 have grabbed onto the tissue and are bunching it together. This apparatus can be continually monitored by medical professionals throughout the procedure.

In a step 208, irrigation and aspiration control port 135 is manipulated so as to exude a cooling liquid such as sterile water, saline, or glycerin from the aperture 118 into the lower region of the bladder. This cooling fluid lowers the relative temperature of the targeted tissues and prevents collateral thermal damage. In alternative embodiments, temperature regulators may include other devices coupled to the apparatus port 132 to chill the cooling fluid or to cause sonic cooling, gas expansion, magnetic cooling or other cooling methodologies. The choice of cooling fluid or methodology is responsive to judgments by medical personnel.

In a step 209, electrodes 119 are selected using the electrode selection and control switch 134. In a preferred embodiment, all electrodes are deployed at once. In another preferred embodiment, electrodes may be individually selected. This step may be repeated at any time prior to step 217.

In a step 210, suction apparatus is coupled to the irrigation and aspiration control ports 135 so that suction may be effected through the irrigation and aspiration ports 124. The tissue surrounding the treatment element 114 may be aspirated so as to conform it to the treatment element 114. The aspiration also removes excess cooling fluid that was supplied in step 209.

In a step 211, the therapeutic energy port 136 is manipulated so as to cause a release of energy from the electrodes 119. The duration and frequency of energy are responsive to judgments by medical personnel. This release of energy creates a pattern of lesions in the mucosal and submucosal tissues of the trigone region. The affected area shrinks and is relatively strengthened, so as to better retain urine. Alternatively, a different method of treatment can be effected by partially or completely ablating nerves responsible for the sensation of urinary urgency.

In a step 212, the catheter 110 is repositioned so that the treatment element 114 is closer to the bladder neck. Prior to repositioning the catheter 110, the electrodes 119 are either retracted or covered by the introducer sheath 116 to prevent unintended damage to tissue while the catheter is being moved.

In a step 213, the energy port 137 is manipulated so as to cause a release of energy from the electrodes 119. The duration and frequency of energy are responsive to judgments by medical personnel. This release of energy creates another pattern of lesions in the mucosal and submucosal tissues of the trigone area. The affected tissue shrinks and is relatively strengthened, so as to better retain urine. By creating a selective pattern of lesions in various areas as in steps 211 and 215, the three-dimensional modeling of the trigone area can be affected. Alternatively, a different method of treatment can be effected by partially or completely ablating nerves responsible for the sensation of urinary urgency.

In a step 214, the catheter 110 is repositioned for a final time so that the treatment element 114 is immediately adjacent to the bladder neck. Prior to repositioning the catheter 110, the electrodes 119 are either retracted or covered by the introducer sheath 116 to prevent unintended damage to tissue while the catheter is being moved.

In a step 215, the energy port 137 is manipulated so as to cause a release of energy from the electrodes 119. The duration and frequency of energy are responsive to judgments by medical personnel. This release of energy creates another pattern of lesions in the submucosal and mucosal tissues around the bladder neck. The affected tissue shrinks and is relatively strengthened, so as to better retain urine. Taken together with the lesions, created in step 211, and 213, the trigone area has been completely remodeled so that the bladder has shrunk and resuspended itself. The relative pressure on the bladder neck is relieved. The scar tissue created by application of the energy is stronger and better able to resist abdominal pressure on the sphincter.

In a step 216, the irrigation and aspiration control port 135 is manipulated so as to stop the flow of cooling liquid from the aperture 118.

In a step 217, pharmaceutical agents may be locally administered by manipulating the irrigation and aspiration control ports 135. These agents may help include lubricants, anesthetics, anti-spasmodics, anti-inflammatories, antiobiotics or other agents as deemed appropriate by the judgment of medical personal. This step may occur any time prior to withdrawal of the catheter 110, to either pretreat tissue or post treat tissues.

In a step 218, the catheter 110 is withdrawn from the urethra.

Figure 3:
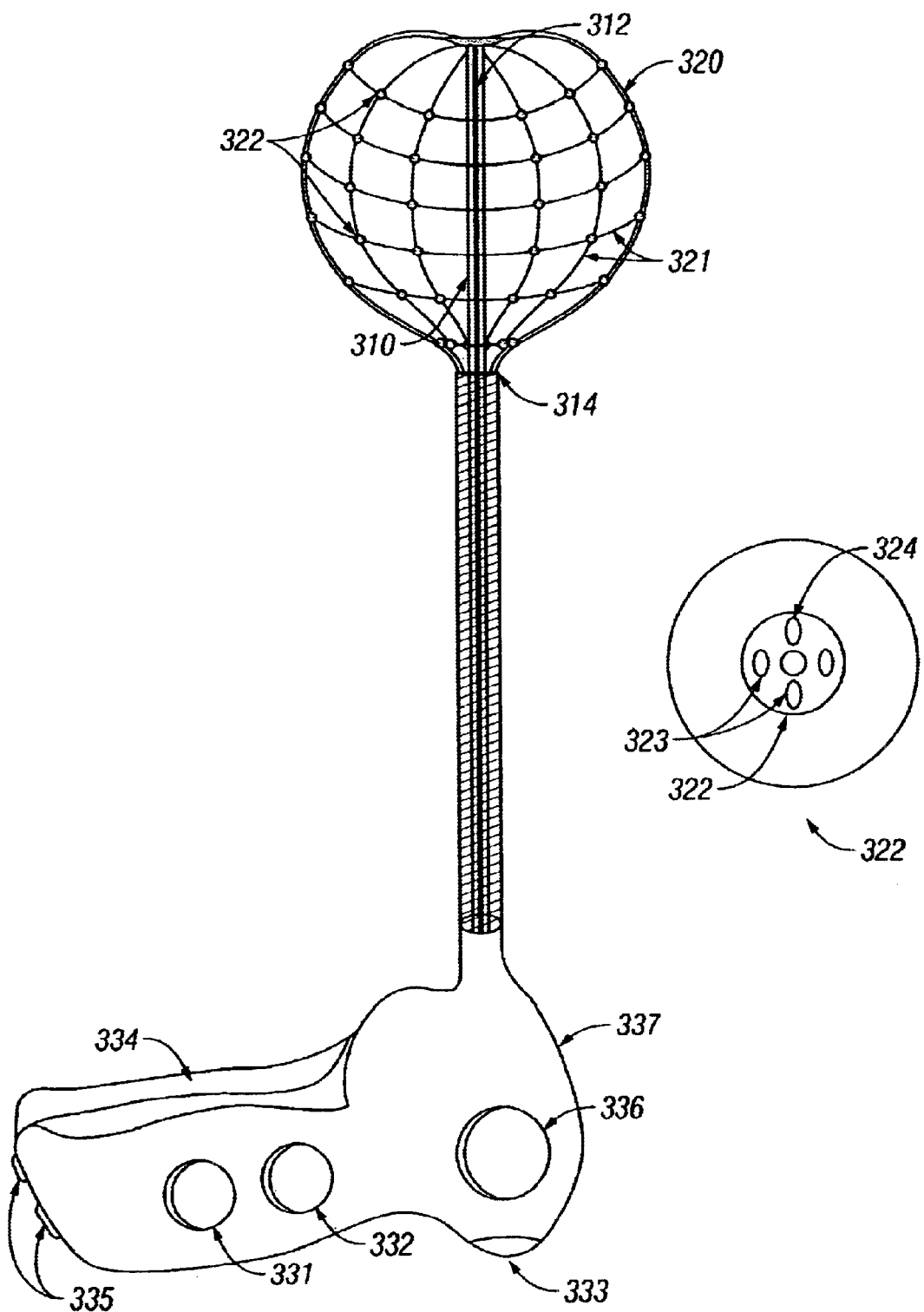
FIG. 3 is a block drawing of a system for treatment of female urinary incontinence using a second device.

FIG. 3 is a block drawing of a system for treatment of female urinary incontinence using a second device.

A system 300 includes a catheter 310, a microporous treatment balloon 320, a control assembly 330 and a shielding element 340 (not shown). In an alternative embodiment, the shielding element 340 is not present.

The Catheter 310

The catheter 310 includes two or more lumens 311 (not shown) and a translation member 312. The two or more lumens 311 and translation member 312 traverse the entire interior length of the catheter 310. The catheter 310 and lumens 311 are coupled at a distal end to a treatment balloon 320; they are coupled at a proximal end to a control assembly 330. The translation member 312 is coupled to the distal end of the treatment balloon 320; it is coupled at the proximal end to a control assembly 330.

In a preferred embodiment, the catheter 310 and treatment balloon 320 are introduced into cavity of the body, such as a female urethra and bladder using an introducer sheath 313 or a guide tube 314. In alternative embodiments, the cavity may include one or more of, or some combination of the following:

- Any portion of the bronchial system, the cardiovascular system, the genito-urinary tract, the lymphatic system, the pulmonary system, the vascular system, the locomotor system, the reproductive system or other systems in the body;
- Any biological conduit or tube, such as a biologic lumen that is patent or one that is subject to a stricture;
- Any biologic operational structure, such as a gland, or a muscle or other organ (such as the colon, the diaphragm, the heart, a uterus, a kidney, a lung, the rectum an involuntary or voluntary sphincter);
- Any biologic structure, such as a herniated body structure, a set of diseased cells, a set of displastic cells, a surface of a body structure, (such as the sclera) a tumor, or a layer of cells (such as fat, muscle or skin).
- Any biologic cavity or space or the contents thereof, such as a cyst, a gland, a sinus, a layered structure, or a medical device implanted or inserted in the body;

The Microporous Treatment Balloon 320

The microporous treatment balloon 320 is comprised of a relatively flexible and heat resistant material such as Kevlar, polyurethane, polyvinyl chloride (PVC), polyamide, PET, nylon or other materials. The shape of the balloon can be manipulated by varying the degree of inflation and the amount of tension placed on the translation member 312. By varying the degree of inflation and the tension on the translation member, the surface of the treatment balloon can be brought in contact with the entire interior surface of the muscles, including the detruser muscles and the top of the bladder. In this way, it is possible to treat the entire organ simultaneously.

The treatment balloon 320 also includes a flexible basket-like structure 321 and a set of surface electrodes 322. The basket-like structure 321 has horizontal and vertical members that completely encompass the balloon 320. The set of surface electrodes 322 are evenly distributed on all the members of the basket-like structure 321. Each electrode 322 includes a sensor 323 to measure temperature, pressure, impedance, flow, nervous activity, pH, conductivity or other property of the tissue or treatment. Each surface electrode 322 is also coupled to a radiopaque marker 324 for use in fluoroscopic visualization.

In an alternative embodiment, the surface electrodes 322 and sensors 323 are embedded directly into the exterior surface of the microporous treatment balloon 320. In this preferred embodiment, the basket-like structure 321 is optional.

In both the preferred and alternative embodiments, the electrodes 322 can be operated separately or in combination with each other. Treatment can be directed at a single area, several different areas, or the entire interior of a bladder or other orifice by operation of selective electrodes. Different patterns of submucosal lesions, mucosal lesions, ablated, bulked or plumped, desiccated or necrotic regions can be created by selectively operating different electrodes. Production of different patterns of treatment makes it possible to remodel tissues and alter their overall geometry with respect to each other.

Each electrode 322 can be disposed to treat tissue by delivering one or more of, or some combination or any of the following in either a unipolar or bipolar mode:

- Radiofrequency (RF) energy, such as RF in about the 300 kilohertz to 500 kilohertz range;
- Chemical treatments, such as acids, antibiotics, enzymes, radioactive tracers or other bioactive substances;
- Infrared energy, such as from an infrared laser or diode laser;
- Microwave energy, such as electromagnetic energy in about the 915 megahertz or 2.45 gigahertz range;
- Sonic energy, including ultrasound;
- Photodynamic therapy (PDT)
- Non-infrared laser energy
- Cryothermia In addition to treating tissues by delivering energy, the set of electrodes 322 and the micropores in the balloon 320 are disposed to deliver at least one flowable substance to the area of the body where treatment is to take place. In a preferred embodiment, the flowable substance includes sterile water, which aids in cooling and hydration of body structures. In other preferred embodiments, the flowable substance includes saline with a concentration of less than about 10% NaCl, which locally enhances tissue conductivity, resulting in a selective areas of ablation or creation of thermal lesions at or below the surface of the tissue. However, in alternative embodiments, the deliverable flowable liquids include other substances, including anesthetic drugs, antiinflammatory agents, chemotherapeutic agents, systemic or topical antibiotics, collagen and radioactive substances such as labeled tracers. In other alternative embodiments, the sensors on the electrodes are used for mapping the foci or pathways of electrical activity in the bladder, the bladdemeck or urethra. This information is used to guide delivery of energy.

In other alternative embodiments, the balloon 320 is not microporous. In this alternative embodiment, electrodes 322 or other energy delivery devices may be mounted upon or proximate to a surface of the balloon.

The Control Assembly 330

The control assembly 330 includes a visualization port 331, an apparatus port 332, an electrical energy port 333, an electrode selection and control switch 334, one or more irrigation and aspiration control ports 335, an therapeutic energy port 336 and a handle 337.

The visualization port 331 can be coupled to visualization apparatus, such as a fiberoptic device, a flouroscopic device, an anoscope, a laparoscope, an endoscope or other type of catheter.

The apparatus port 332 can be coupled to other medical devices that may be useful during treatment such as a pH meter, a pressure monitor, drug administration apparatus, or other devices used to monitor or treat the patient.

In a preferred embodiment, devices coupled to both the visualization port 331 and the apparatus ports 332 are controlled from a location outside the body, such as by an instrument in an operating room or an external device for manipulating the inserted catheter 310.

In an alternative embodiment the apparatus port 332 may be coupled to devices that are implanted or inserted into the body during a medical procedure. For example, the apparatus port 332 may be coupled to a programmed AICD (artificial implanted cardiac defibrillator), a programmed glandular substitute (such as an artificial pancreas) or other device for use during surgery or other medical procedures.

The electrical energy port 333 includes a conductive element such as an electrical adapter that can be coupled to a source of alternating or direct current such as a wall socket, battery or generator.

The electrode selection and control switch 334 includes an element that is disposed to select and activate individual electrodes 322.

The irrigation and aspiration control ports 335 can be coupled to a pump or other apparatus to inflate or deflate the balloon and deliver fluids through the micropores of the treatment balloon 320.

The therapeutic energy port 336 includes a receptor port for coupling to a source of any of the following types of therapeutic energy:

Radiofrequency (RF) energy, such as RF in about the 300 kilohertz to 500 kilohertz range;
Chemical treatments, such as acids, antibiotics, enzymes, radioactive tracers or other bioactive substances;
Infrared energy, such as from an infrared laser or diode laser;
Microwave energy, such as electromagnetic energy in about the 915 megahertz or 2.45 gigahertz range;
Sonic energy, including ultrasound;
Photodynamic therapy (PDT)
Non-infrared laser energy
Cryothermia The handle 337 is disposed for manipulated by medical or veterinary personnel and can be shaped for being held in the hand. The visualization port 331, the apparatus port 332, the electrical energy port 333, the electrode selection and control switch 334 and the one or more irrigation and aspiration control ports 335 and the therapeutic energy port 336 are all mounted in the handle 337 to allow for easy operation.

The Shielding Element 340

The shielding element 340 lies on the proximal side of the microporous treatment balloon 320 and is disposed to isolate the treatment area. It can also help position the catheter 310 in the body. For example, in a preferred embodiment in which the catheter 310 is inserted into the urethra, the shielding element 340 can prevent the catheter 310 from being inserted further into the urethral canal or bladder and prevent substances used in treatment from escaping. In an alternative embodiment, the shielding element 340 is optional.

Figure 4A:
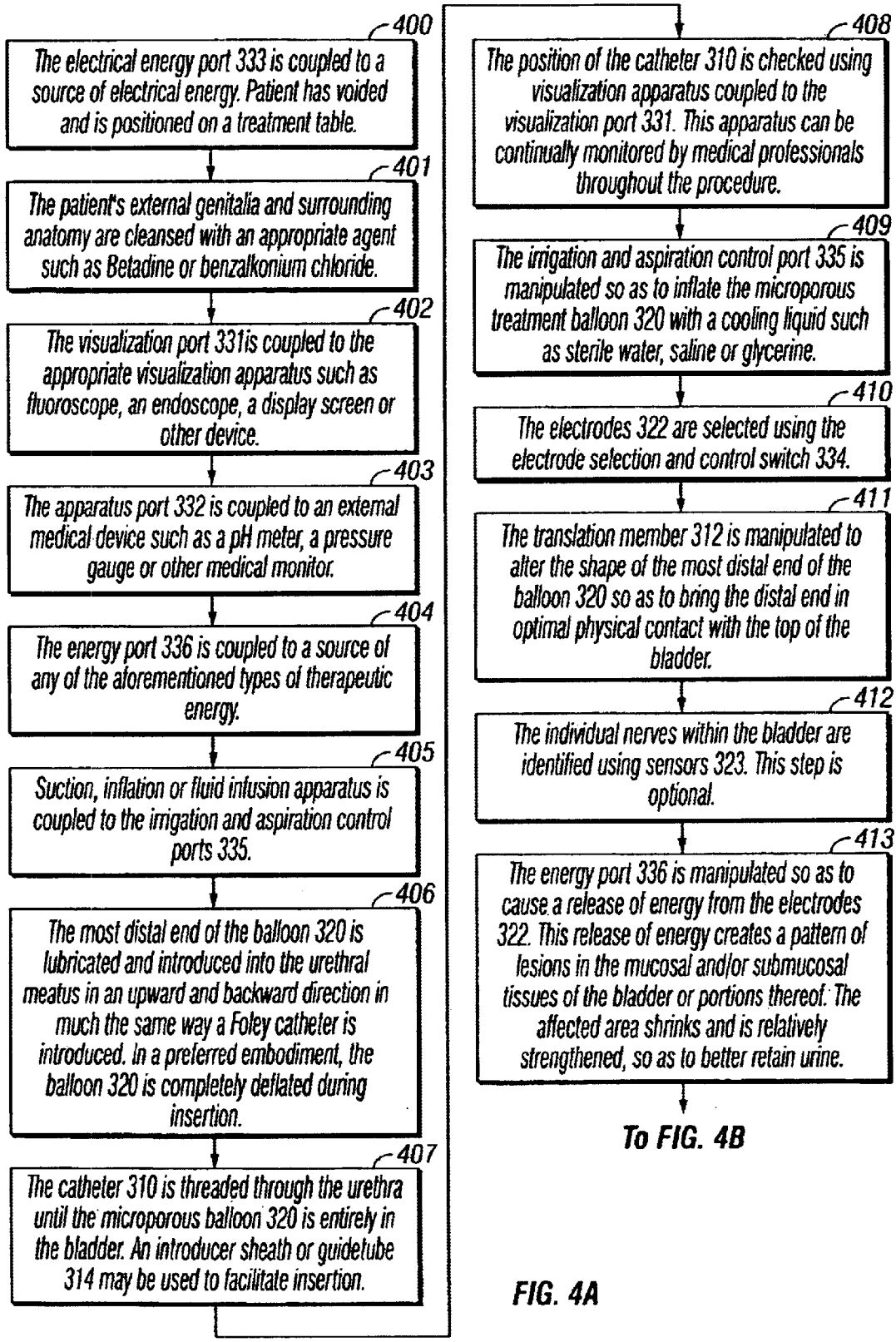
FIG. 4 is a process flow drawing of a method for treatment of female urinary incontinence using a second device.

FIG. 4 is a process flow drawing of a method for treatment of female urinary incontinence using a second device.

A method 400 is performed by a system 300 including a catheter 310, a treatment balloon 320 and a control assembly 330. Although the method 400 is described serially, the steps of the method 400 can be performed by separate elements in conjunction or in parallel, whether asynchronously, in a pipelined manner, or otherwise. There is no particular requirement that the method 400 be performed in the same order in which this description lists the steps, except where so indicated.

At a flow point 400, electrical energy port 333 is coupled to a source of electrical energy. The patient has voided and is positioned on a treatment table, in an appropriate position such as horizontal, jackknife or lithotomy. Due to the potential for inducing pain, the area surrounding the urinary meatus may be pretreated with a topical anesthetic before insertion of the catheter 310; depending upon the circumstances, a muscle relaxant or short term tranquilizer may be indicated. The position of the patient and choice of pharmaceutical agents to be used are responsive to judgments by medical personnel.

At a step 401, the patient's external genitalia and surrounding anatomy are cleansed with an appropriate agent such as Betadine, or benzalkonium chloride.

At a step 402, the visualization port 431 is coupled to the appropriate visualization apparatus, such as a flouroscope, an endoscope, a display screen or other visualization device. The choice of visualization apparatus is responsive to judgments by medical personnel.

At a step 403, the apparatus port 332 is coupled to an external medical device such as a pH meter, a pressure gauge, or other medical equipment. The choice of apparatus is responsive to judgments by medical personnel.

At a step 404, the therapeutic energy port 336 is coupled to a source of any of the aforementioned types of therapeutic energy.

In a step 405, suction, inflation or fluid infusion apparatus is coupled to the irrigation and aspiration control ports 335 so that the treatment balloon may be later be inflated and deflated and substances may be administered.

At a step 406, the most distal end of the treatment balloon 320 is lubricated and introduced into the urethral meatus in an upward and backward direction, in much the same way a Foley catheter is introduced. The choice of lubricant is responsive to judgments by medical personnel. In a preferred embodiment, the balloon 320 is completely deflated during insertion.

In a step 407, the catheter 310 is threaded through the urethra until the microporous balloon 320 has completely passed the bladderneck and is entirely in the bladder. An introducer sheath 313 or guidetube 314 may also be used to facilitate insertion.

In a step 408, the position of the catheter 310 is checked using visualization apparatus coupled to the visualization port 331. This apparatus can be continually monitored by medical professionals throughout the procedure.

In a step 409, the irrigation and aspiration control port 335 is manipulated so as to inflate the microporous treatment balloon 320. In a preferred embodiment, the treatment balloon 320 is inflated with a cooling liquid such as sterile water, saline or glycerin. This cooling fluid lowers the relative temperature of the targeted tissues that are in physical contact and prevents collateral thermal damage. In alternative embodiments, other devices may be coupled to the apparatus port 132 to chill the cooling fluid or cause sonic cooling, gas expansion, magnetic cooling or others cooling methodologies. The choice of cooling fluid or methodology is responsive to judgments by medical personnel.

In a step 410, electrodes 322 are selected using the electrode selection and control switch 334.

In a step 411, the translation member 312 is manipulated to alter the shape of the most distal end of the balloon so as to bring the distal end of the balloon in optimal physical contact with the top of the bladder.

In a step 412, individual nerves within the bladder are identified using sensors 323. This step is optional.

In a step 413, the therapeutic energy port 336 is manipulated so as to cause a release of energy from the electrodes 322. The duration and frequency of energy are responsive to judgments by medical personnel. This release of energy creates a pattern of lesions in the mucosal or submucosal tissues of the bladder or portions thereof. The affected area shrinks and is relatively strengthened, so as to better retain urine.

In a step 414, the therapeutic energy port 336 is manipulated so as to cause a release of energy from the electrodes 322 that is directed at the nerves that were identified in step 412. Manipulation and modulation of these nerves may directly or indirectly affect incontinence related to an uncontrolled urge to urinate. This step is optional.

In a step 415, bulking agents such as organic microspheres, collagens, silicone, PVC and other organic breathable and unbreathable polymers are exuded from selected electrodes 322 positioned near the base of the bladder. The type of microspheres and bulking substances and the locations where they are exuded are responsive to judgment by medical personnel. These bulking agents can be used to strengthen these structures so as to prevent incontinence caused by stress.

In a step 416, pharmaceutical agents may be locally administered by manipulating the irrigation and aspiration control ports 335. These agents may help include lubricants, anesthetics, anti-spasmodics, anti-inflammatories, antibiotics or other agents as deemed appropriate by the judgment of medical personal. This step may occur any time prior to withdrawal of the catheter 310, to either pretreat tissue or post-treat tissues.

In a step 417, the irrigation and aspiration control port 335 is manipulated so as to reverse the flow of cooling liquid into the microporous treatment balloon 320 and cause it to deflate.

In a step 418, the catheter 310 is withdrawn from the urethra.

Figure 5:
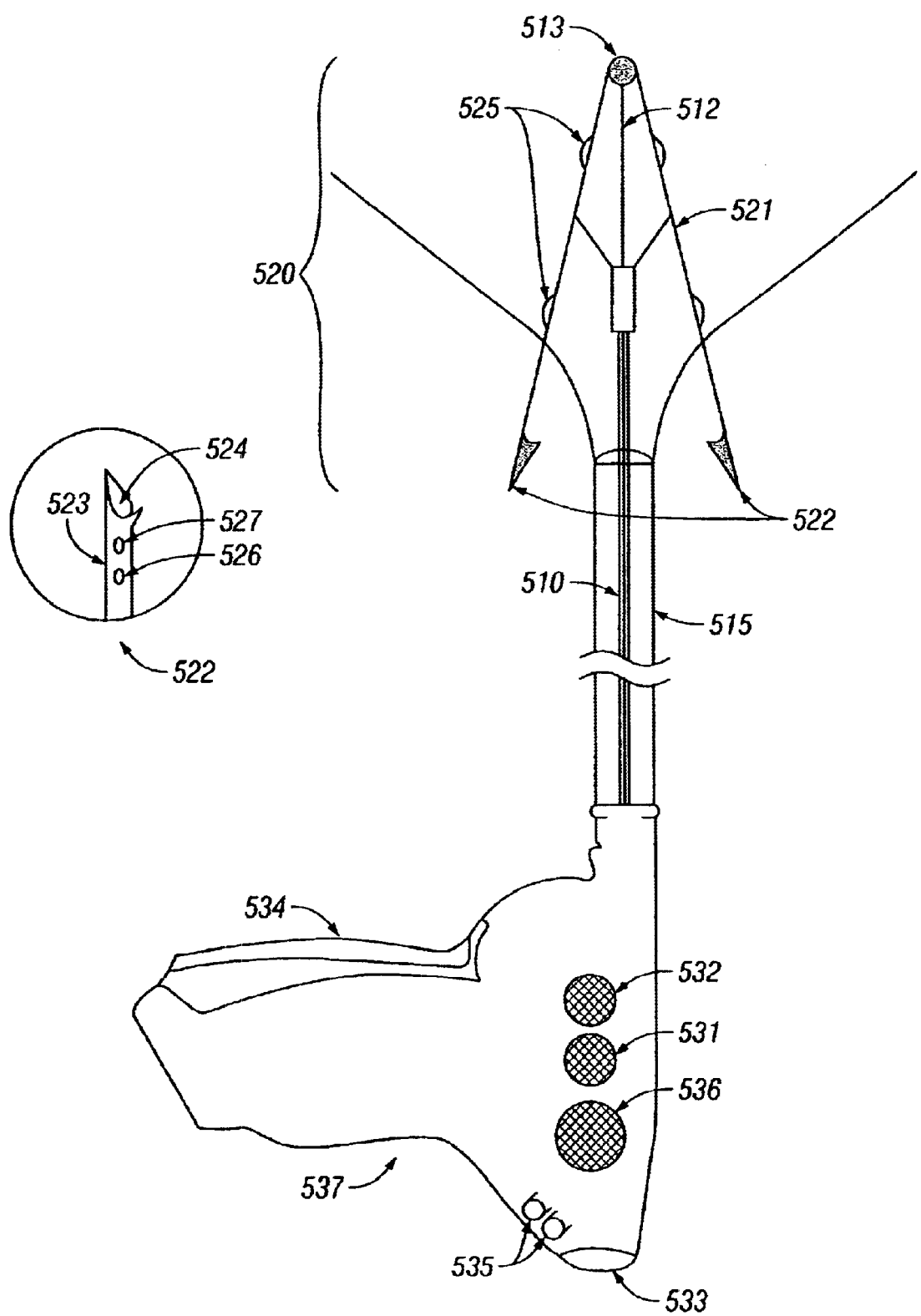
FIG. 5 is a block drawing of a system for treatment of female urinary incontinence using a third device.

FIG. 5 is a block drawing of a system for treatment of female urinary incontinence using a third device.

A system 500 includes a catheter 510, treatment element 520, a control assembly 530 and a shielding element 540. In an alternative embodiment, the shielding element 540 is not present.

The Catheter 510

The catheter 510 includes two or more lumens 511, a translation member 512 and a tapered tip 513. The lumens 511 and translation member 512 run the entire interior length of the catheter 510. The proximal end of the lumens 511 is coupled to the control assembly 530; the distal end of the lumens 511 is coupled to the treatment element 520. It is through these lumens 511 that energy is conducted and flowable substances are exuded. The proximal end of the translation member 512 is coupled to the control assembly 530; the distal end of the translation member 512 is coupled to the taper tip 513.

In a preferred embodiment, the tapered tip 513 is rigid so as to allow easy insertion into a urethra. In other preferred embodiments, the tapered tip 513 may be of varying degrees of flexibility depending where it in the body it is deployed. In alternative embodiments, the catheter 510 may be introduced into the target tissue using an introducer sheath 514 or a guide wire 515.

In a preferred embodiment, the tapered tip 513 is disposed for insertion into a cavity of the body such as a female urethra and bladder. In alternative embodiments, the cavity may include one or more of, or some combination of the following:

Any portion of the bronchial system, the cardiovascular system, the genito-urinary tract, the lymphatic system, the pulmonary system, the vascular system, the locomotor system, the reproductive system or other systems in the body;

Any biological conduit or tube, such as a biologic lumen that is patent or one that is subject to a stricture;

Any biologic operational structure, such as a gland, or a muscle or other organ (such as the colon, the diaphragm, the heart, a uterus, a kidney, a lung, the rectum an involuntary or voluntary sphincter);

Any biologic structure, such as a herniated body structure, a set of diseased cells, a set of displastic cells, a surface of a body structure, (such as the sclera) a tumor, or a layer of cells (such as fat, muscle or skin);

Any biologic cavity or space or the contents thereof, such as a cyst, a gland, a sinus, a layered structure, or a medical device implanted or inserted in the body.

The Treatment Element 520

The treatment element 520 includes a set of umbrella-like struts 521, a set of electrodes 522, a set of irrigation and aspiration ports 525 and a set of sensors 526.

The set of umbrella like struts 521 are several centimeters long. One end of the struts 521 is not attached to any part of the device. The other end of the strut 521 is coupled to the distal end of the translation member 512 at the tapered tip 513 in such a way that when tension is applied to the proximal end of the translation member 512, the umbrella-like struts 521 open up in much the same way as an umbrella.

A set of electrodes 522 are evenly distributed on the outer surface of each strut 521. Each free-floating end of a strut 521 includes at least one electrode 522. Each electrode 522 includes a metallic tube 523 defining a hollow lumen 524. In a preferred embodiment, the set of electrodes 522 are needle electrodes; other preferred embodiments include surface electrodes or a combination of needle electrodes and surface electrodes.

Each electrode 522 is coupled to at least one sensor 526 capable of measuring such factors as temperature, conductivity, pressure, impedance and other variables. In a preferred embodiment, each electrode 522 is also coupled to a radiopaque marker 527 for use in fluoroscopic visualization.

In a preferred embodiment, the electrodes 522 can be operated separately or in combination with each other. Treatment can be directed at a single area or several different areas of a bladder or other orifice by operation of selected electrodes. Different patterns of submucosal lesions, mucosal lesions, ablated, bulked, plumped, desiccated or necrotic regions can be created by selectively operating different electrodes. Production of different patterns of treatment makes it possible to remodel tissues and alter their overall geometry with respect to each other.

Each electrode 522 can be disposed to treat tissue by delivering one or more of, or some combination or any of the following in either a unipolar or bipolar mode:

Radiofrequency (RF) energy, such as RF in about the 300 kilohertz to 500 kilohertz range;

Chemical treatments, such as acids, antibiotics, enzymes, radioactive tracers or other bioactive substances;

Infrared energy, such as from an infrared laser or diode laser;

Microwave energy, such as electromagnetic energy in about the 915 megahertz or 2.45 gigahertz range;

Sonic energy, including ultrasound;

Photodynamic therapy (PDT)

Non-infrared laser energy

Cryothermia

In addition to treating tissues by delivering energy, the set of electrodes 522 are disposed to deliver at least one flowable substance to the area of the body where treatment is to take place. In a preferred embodiment, the flowable substance includes sterile water which aides in cooling and hydration of body structures. In another preferred embodiment, the flowable substance includes saline with a concentration of less than about 10% NaCl. Saline is used to increate the local conductivity of tissue, enhancing the penetration of RF energy so as to create larger lesions. The saline can be delivered through the needle electrode submucosally so as to achieve greatest effect. However, in alternative embodiments, the deliverable flowable liquids include other substances, including anesthetic drugs, anti-inflammatory agents, chemotherapeutic agents, systemic or topical antibiotics, collagen and radioactive substances such as labeled tracers.

A set of irrigation and aspiration ports 525 are also evenly distributed on the outer surface of each strut 521. Each free-floating end of a strut 521 also includes at least one irrigation and aspiration port 525. Suction can be applied through these ports so as to bring the targeted tissue in closer physical proximity to the electrodes 522. The irrigation and aspiration ports 525 can also be used to administer cooling fluids in such a way as to minimize thermal damage. Drugs, bulking agents and other flowable substances can be infused through the irrigation and aspiration ports 525.

The Control Assembly 530

The control assembly 530 includes a visualization port 531, an apparatus port 532, an electrical energy port 533, an electrode selection and control switch 534, one or more irrigation and aspiration control ports 535, an therapeutic energy port 536 and a handle 537.

The visualization port 531 can be coupled to visualization apparatus, such as a fiberoptic device, a flouroscopic device, an anoscope, a laparoscope, an endoscope or other type of catheter.

The apparatus port 532 can be coupled to other medical devices that may be useful during treatment such as a pH meter, a pressure monitor, drug administration apparatus, or other device used to monitor or treat the patient.

In a preferred embodiment, devices coupled to both the visualization port 531 and the apparatus ports 532 are controlled from a location outside the body, such as by an instrument in an operating room or an external device for manipulating the inserted catheter 510.

In an alternative embodiment the apparatus port 532 may be coupled to devices that are implanted or inserted into the body during a medical procedure. For example, the apparatus port 532 may be coupled to a programmed AICD (artificial implanted cardiac defibrillator), a programmed glandular substitute (such as an artificial pancreas) or other device for use during surgery or other medical procedures.

The electrical energy port 533 includes a conductive element such as an electrical adapter that can be coupled to a source of alternating or direct current such as a wall socket, battery or generator.

The electrode selection and control switch 534 includes an element that is disposed to select and activate individual electrodes 522.

The irrigation and aspiration control ports 535 can be coupled to a pump or other apparatus to deliver fluid through the irrigation and aspiration ports 525 or electrodes 522 or to apply suction through the set of irrigation and aspiration ports 525.

The therapeutic energy port 536 includes a receptor port for coupling to a source of any of the following types of therapeutic energy:

Radiofrequency (RF) energy, such as RF in about the 300 kilohertz to 500 kilohertz range;

Chemical treatments, such as acids, antibiotics, enzymes, radioactive tracers or other bioactive substances;

Infrared energy, such as from an infrared laser or diode laser;

Microwave energy, such as electromagnetic energy in about the 915 megahertz or 2.45 gigahertz range;

Sonic energy, including ultrasound;

Photodynamic therapy (PDT)

Non-infrared laser energy

Cryothermia

The handle 537 is disposed for manipulated by medical or veterinary personnel and can be shaped for being held in the hand. The visualization port 531, the apparatus port 532, the electrical energy port 533, the electrode selection and control switch 534 and the one or more irrigation and aspiration control ports 535 and the therapeutic energy port 536 are all mounted in the handle 537 to allow for easy operation.

The Shielding Element 540

The shielding element 540 lies on the proximal side of treatment element 520 and is disposed to isolate the treatment area. It can also help position the catheter 510 in the body. For example, in a preferred embodiment in which the catheter 510 is inserted into the urethra, the shielding element 540 can prevent the catheter 510 from being inserted further into the urethral canal and prevent substances used in treatment from escaping. In an alternative embodiment, the shielding element 540 is optional.

Figure 6A:
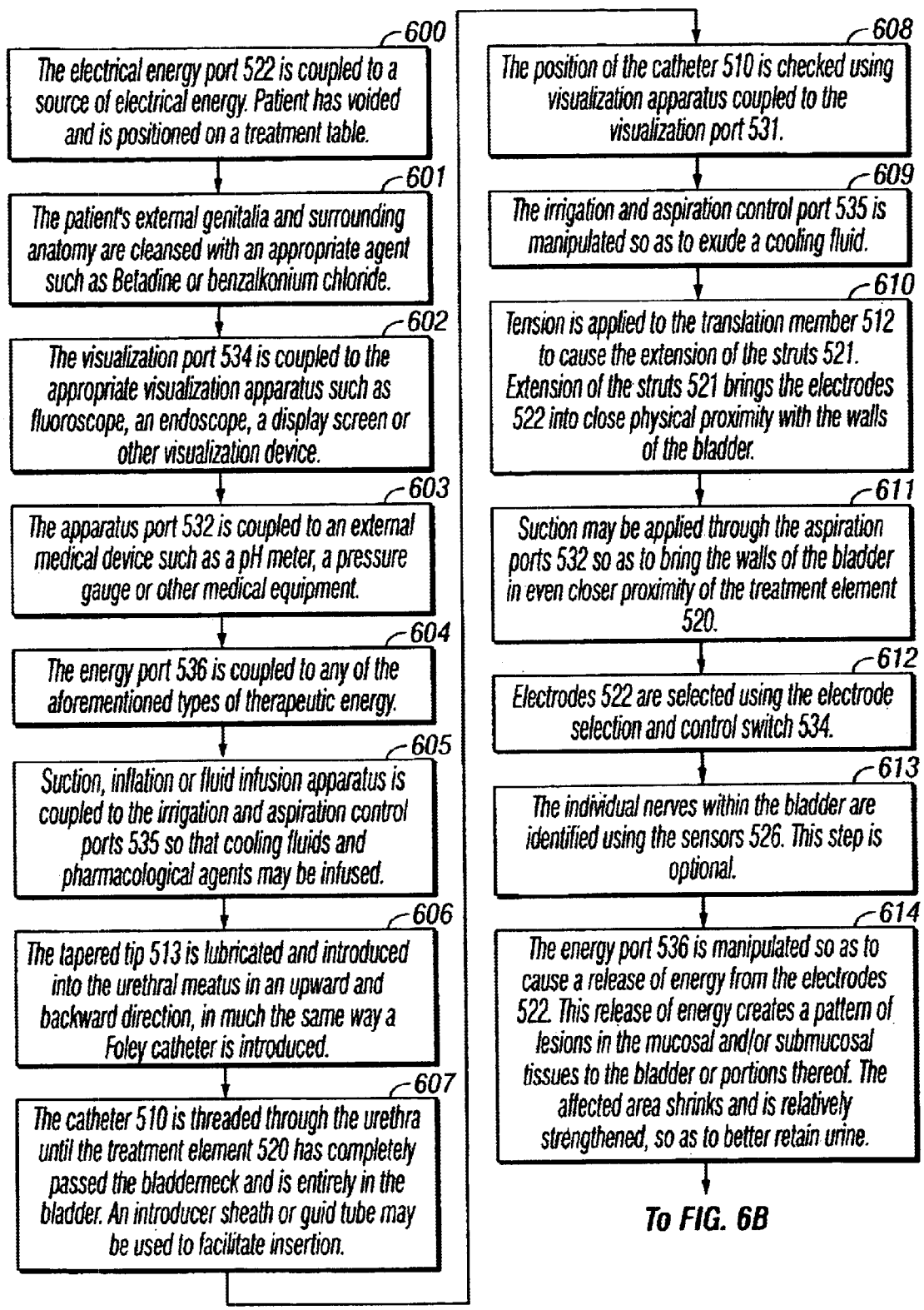
FIG. 6 is a flow drawing of a method for treatment of female urinary incontinence using a third device.

FIG. 6 is a process flow drawing of a method for treatment of female urinary incontinence using a third device. Although the method 600 is described serially, the steps of the method 600 can be performed by separate elements in conjunction or in parallel, whether asynchronously, in a pipelined manner, or otherwise. There is no particular requirement that the method 600 be performed in the same order in which this description lists the steps, except where so indicated.

A method 600 is performed by a system 500 including a catheter 510, a treatment element 520 and a control assembly 530.

At a flow point 600, electrical energy port 533 is coupled to a source of electrical energy. The patient has voided and is positioned on a treatment table, in an appropriate position such as horizontal, jackknife or lithotomy. Due to the potential for inducing pain, the area surrounding the urinary meatus may be pretreated with a topical anesthetic before insertion of the catheter 510; depending upon the circumstances, a muscle relaxant or short term tranquilizer may be indicated. The position of the patient and choice of pharmaceutical agents to be used are responsive to judgments by medical personnel.

At a step 601, the patient's external genitalia and surrounding anatomy are cleansed with an appropriate agent such as Betadine, or benzalkonium chloride.

At a step 602, the visualization port 531 is coupled to the appropriate visualization apparatus, such as a flouroscope, an endoscope, a display screen or other visualization device. The choice of visualization apparatus is responsive to judgments by medical personnel.

At a step 603, the apparatus port 532 is coupled to an external medical device such as a pH meter, a pressure gauge, or other medical equipment. The choice of apparatus is responsive to judgments by medical personnel.

At a step 604, the therapeutic energy port 536 is coupled to a source of any of the aforementioned types of therapeutic energy.

In a step 605, suction, inflation or fluid infusion apparatus is coupled to the irrigation and aspiration control ports 535 so that cooling fluids and pharmacological agents may be administered.

At a step 606, the tapered tip 513 is lubricated and introduced into the urethral meatus in an upward and backward direction, in much the same way a Foley catheter is introduced. The choice of lubricant is responsive to judgments by medical personnel. In a preferred embodiment, the treatment element 520 is completely closed to facillitate insertion.

In a step 607, the catheter 510 is threaded through the urethra until the treatment element 520 has completely passed the bladderneck and is entirely in the bladder. An introducer sheath 513 or guidetube 514 may also be used to facilitate insertion.

In a step 608, the position of the catheter 510 is checked using visualization apparatus coupled to the visualization port 531. This apparatus can be continually monitored by medical professionals throughout the procedure.

In a step 609, the irrigation and aspiration control port 535 is manipulated so as to exude a cooling fluid. In a preferred embodiment, the cooling fluid may include sterile water, saline or glycerin. This cooling fluid lowers the relative temperature of the targeted tissues that are in physical and prevents collateral thermnal damage. In alternative embodiments, other devices may be coupled to the apparatus port 532 to chill the cooling fluid or cause sonic cooling, gas expansion, magnetic cooling or others cooling methodologies. The choice of cooling fluid or methodology is responsive to judgments by medical personnel.

In a step 610, tension is applied to the translation member 512 to cause extension of the struts 522. Extension of the struts 522 brings the electrodes 522 into physical proximity with the walls of the bladder.

In a step 611, the irrigation and aspiration control ports 535 are manipulated so as to apply suction through the irrigation and aspiration ports 525 and bring the walls of the bladder in even closer proximity to the treatment element 520.

In a step 612, electrodes 522 are selected using the electrode selection and control switch 534. In a preferred embodiment, all electrodes are selected. In another embodiment, individual electrodes may be deployed.

In a step 613, individual nerves within the bladder are identified using sensors 526. This step is optional.

In a step 614, the therapeutic energy port 536 is manipulated so as to cause a release of energy from the electrodes 522. The duration and frequency of energy are responsive to judgments by medical personnel. This release of energy creates a pattern of lesions in the mucosal and/or submucosal tissues of the bladder or portions thereof. The affected area shrinks and is relatively strengthened, so as to better retain urine.

In a step 615, the therapeutic energy port 536 is manipulated so as to cause a release of energy from the electrodes 522 that is directed at the nerves that were identified in step 613. Manipulation and modulation of these nerves may directly or indirectly affect incontinence related to an uncontrolled urge to urinate. This step is optional.

In a step 616, bulking agents such as organic microspheres, collagens, silicone, PVC and other organic breathable and unbreathable polymers are exuded from selected electrodes 522 into tissues near the base of the bladder. The type of microspheres and bulking substances and the locations where they are exuded are responsive to judgment by medical personnel. These bulking agents can be used to strengthen these structures so as to prevent incontinence caused by stress. This step is optional.

In a step 617, pharmaceutical agents may be locally administered by manipulating the irrigation and aspiration control ports 535. These agents may help include lubricants, anesthetics, anti-spasmodics, anti-inflammatories, antiobiotics or other agents as deemed appropriate by the judgment of medical personal. This step may occur any time prior to withdrawal of the catheter 510, either to pre-treat tissue or post-treat tissues.

In a step 618, the irrigation and aspiration control port 535 is manipulated so as to reverse the flow of cooling liquid.

In a step 619, tension is applied to the translation member 512 to cause the umbrella like struts 521 to collapse and close around the catheter 510.

In a step 620, the catheter 510 is withdrawn from the urethra.

Generality of the Invention

The invention has substantial generality of application to various fields for biopsy or treatment of medical conditions. These various fields include, one or more of, or a combination of, any of the following (or any related fields):

As noted above, the invention can be used in any area of the body, including the biologic systems and locations noted herein. The invention can be used for the general purpose of reducing, plumping, or reshaping body structures, tissues, or regions of the body otherwise empty (or filled with biologic substances).

For examples, the invention can be used in one or more of, or some combination of, the following:

In the head and neck, such as the cheeks, eyes, sinuses, middle ear, nostrils, inner ear, Eustachian tubes, pharynx, larynx, or other structures;

For the purpose of reforming damaged body parts, for the purpose of reshaping misshapen body parts, dilating occluded tissues, or for cosmetic effects; or For the purpose of replacing the volume filled by body parts that are missing, whether due to congenital defect, infection, or surgery.

Alternative embodiments

Although preferred embodiments are disclosed herein, many variations are possible which remain within the concept, scope, and spirit of the invention, and these variations would become clear to those skilled in the art after perusal of this application.

What is claimed is:

1. Apparatus comprising:

a catheter disposed for insertion into a body at a selected location, said catheter including a treatment element coupled at a distal end of said catheter; and a set of electrodes coupled proximately to said treatment element, said electrodes being adapted to deliver energy and chemical treatment; and an element for selecting and activating said electrodes by an operator, individually or as sequences of electrodes disposed in arrays.

2. Apparatus as in claim 1, wherein said catheter includes at least one irrigation and aspiration port capable of aspirating tissue and delivering substances.

3. Apparatus as in claim 1, wherein at least one electrode is coupled to a heat resistant inflatable balloon.

4. Apparatus in claim 1, wherein a pullwire can be disposed to alter the shape of said heat resistant inflatable balloon.

5. Apparatus as in claim 1, wherein at least one electrode is mounted to at least one umbrella-like strut.

6. Apparatus as in claim 4, wherein said pullwire can be disposed to extend said umbrella-like struts.

7. Apparatus as in claim 1, wherein said catheter is disposed for either laparoscopic or manual insertion into said selected location.

8. Apparatus as in claim 1, wherein said applied energy includes one or more of:

RF energy at about 300 to about 500 kilohertz;

photodynamic therapy;

microwave energy in about the 915 megahertz to 2.45 gigahertz range;

sonic energy; and infrared energy;

and wherein said chemical treatment includes one or more of:
enzymes;
acid-base reactions;
radioactive tracers; and
chemical desiccants.

9. Apparatus as in claim 1, including an optional shielding element coupled to said catheter.

10. Apparatus as in claim 9, wherein said optional shielding element includes any of:

an inflatable balloon;

a sponge; and apolymner shield;

wherein said shielding element is disposed to prevent to present a liquid-tight seal in a region proximate to said selected location.

11. Apparatus as in claim 1, including a sensor disposed for delivering electromagnetic energy from said selected location to a location outside said body.

12. Apparatus as in claim 11, wherein said sensor includes at least one of:

an electromagnetic impedance sensor;

an optical sensor;

a conductivity sensor;

a temperature sensor;

a pressure sensor;

a sensor for identifying nervous activity;

a pH sensor; and ardliopaque marker.

13. Aparausas in claim 1, including a temperature ragulator coupled to said catheter.

14. Apparatus as in claim 13, wherein said temperature regulator includes a chilled liquid disposed proximate to said selected location.

15. Apparatus as in claim 1, including at least one lumen for delivering a flowable substance to said selected location, said flowable substance being responsive to said electromagnetic energy.

16. Apparatus as in claim 15, wherein said flowable substance has a selected response to said applied energy, said selected response including receiving said applied energy for one or more of:

ablation;

coating;

expansion;

plumping;

shaping;

bulking;

modulating nervous pathways;

reducing compliance; and shrinldng tissue.

17. Apparatus as in claim 1, wherein said at least one electrode is disposed for coupling to circuits capable of controlled application of said electromagnetic energy within an interior region of a body cavity.

18. Apparatus as in claim 17, wherein said controlled application includes uniform distribution of said electromagnetic energy in said interior region.

19. Apparatus as in claim 1, wherein said catheter includes at least one lumen capable of delivery of a flowable substance from outside the body to said selected location.

20. Apparatus as in claim 19, wherein said flowable substance includes at least one of: a drug, a gas, a radioisotope, an analgesic, an antibiotic, an anti-inflammatory, an anti-spasmodic, a bulking agent such as microbeads suspended in a delivery vehicle or a cooling fluid such as a glycerin or saline.

21. Apparatus as in claim 1, wherein said selected location is disposed within one of a human and an animal subject; and said electromagnetic energy is delivered proximate to said selected location to one or more of:
a sphincter;
muscle tissue; and
nerve tissue.

22. Apparatus as in claim 21, wherein said sphincter or tissue is proximate to one or more of:

a bladder;

esophagus;

uterus;

fallopian tube;

vas deferens;

sinus cavity;

aorta;

larynx; and pharynx.

23. Apparatus as in claim 21, wherein the sphincter or tissue includes one or more of:

trigone area of a bladder;

detruser muscles of a bladder;

bladderneck;

urethra; and nerves that inform any of said trigone area, said detruser muscles, said bladderneck and said urethra.

* * * * *